United States Patent [19]

Lazarus

[11] Patent Number: 5,158,543
[45] Date of Patent: Oct. 27, 1992

[54] LAPAROSCOPIC SURGICAL SYSTEM AND METHOD

[76] Inventor: Harrison M. Lazarus, 324 - 10th Ave., Salt Lake City, Utah 84103

[21] Appl. No.: 605,963

[22] Filed: Oct. 30, 1990

[51] Int. Cl.$^5$ ............................................... A61M 5/00
[52] U.S. Cl. ..................................... 604/164; 606/191
[58] Field of Search ................... 604/51, 52, 53, 158, 604/161, 162, 163, 164, 165, 169, 170; 606/191; 128/4

[56] References Cited

U.S. PATENT DOCUMENTS

| | | | |
|---|---|---|---|
| 4,351,333 | 9/1982 | Lazarus et al. | 604/164 |
| 4,449,532 | 5/1984 | Storz | 128/4 |
| 4,850,960 | 7/1989 | Grayzel | 604/158 |
| 4,862,891 | 9/1989 | Smith | 606/191 |
| 4,869,717 | 9/1989 | Adair | 604/164 |
| 4,978,334 | 12/1990 | Toye et al. | 604/164 |
| 4,981,482 | 1/1991 | Ichikawa | 606/191 |
| 5,002,557 | 3/1991 | Hasson | 606/191 |

*Primary Examiner*—Paul J. Hirsch
*Attorney, Agent, or Firm*—Trask, Britt & Rossa

[57] ABSTRACT

A method for performing laparoscopic surgery involving placing cannulas through the abdominal wall of a patient preparatory to surgery is disclosed. The method includes inserting a needle and blunt-ended guidewire through the abdominal wall until the tip of the needle and the guidewire are positioned within the peritoneal cavity of the patient. A dilator or dilators having tapered ends are threaded over the guidewire until the appropriate size of aperture is created in the peritoneum. The method of the invention provides a safer means of introducing laparoscopic equipment into the peritoneal cavity with reduced incidence of inadvertent punctures to internal organs and vessels. A kit including the necessary components for performing the method is also disclosed.

15 Claims, 7 Drawing Sheets

LAPAROSCOPIC SURGICAL SYSTEM AND METHOD

BACKGROUND

1. Field of the Invention

This invention relates to surgical procedures for placement and positioning of surgical instruments into the abdominal cavity of a patient for the purpose of performing laparoscopic surgical techniques. More specifically, this invention relates to the insertion of insufflation needles and cannulas into the peritoneal cavity of a patient for the purpose of performing laparoscopic surgery.

2. Statement of the Art

Laparoscopy is a surgical technique which has been known in some form for more than seventy years. Laparoscopy is generally a technique whereby the interior of the body may be viewed by means of a scope or other camera-like equipment. In its infancy, laparoscopy was used to map and catalog the pathology of the urinary bladder. Beginning in the latter part of this century, laparoscopy gained significant acceptance as a tool for performing gynecological procedures. It has only been in the past few years, however, that laparoscopy has been adapted for use in other surgical techniques relating to the abdominal region. For example, laparoscopy is now being used for intraperitoneal exploration under conditions which once required more invasive techniques. Laparoscopy is also used now to perform biopsies and necessary surgeries. The use of laparoscopy in other medical procedures is likely to increase in the future as the technique becomes more widely known and used.

Laparoscopy has recently been highlighted as a new means for conducting cholecystectomy. Previously, cholecystectomy surgery required the making of a sizable incision in the abdominal wall, between the costal margin and umbilicus, in order to access the gall bladder. Due to the severity of this surgery, a cholecystectomy patient was typically hospitalized for several days, and recovery was lengthy. With laparoscopic techniques, however, approximately one half of all cholecystectomy patients can be treated under outpatient conditions. Most patients can return to normal activity within a day or two after surgery and are limited only by any abdominal tenderness that may be experienced.

Cholecystectomy by laparoscopy is performed through at least two, and most often four, small incisions made in the abdominal region between the costal margin and umbilicus. Optical equipment and surgical instruments are inserted through the small incisions in order to perform the cholecystectomy.

Laparoscopic surgery is begun by preparing the patient for surgery following techniques well known in the art. The patient is typically given a local anesthetic in the region of the umbilicus to deaden the pain of the incisions. A pneumoperitoneum is created in order to facilitate viewing of and access to the organs. A pneumoperitoneum involves introducing a gas into the peritoneal cavity by a procedure known as insufflation.

Standard insufflation technique involves making a small (approximately 1 centimeter) incision through the dermis of the abdominal wall in close proximity to the umbilicus. The umbilical region presents the best point of entry into the peritoneal cavity because the anterior abdominal wall is thinnest at that point; however, the underlying fascia and peritoneum in the area are tough elastic connective tissues and are very difficult to breach. An apertured needle is then inserted into the incision site. A needle well-known in the art and one which is used widely for the creation of the pneumoperitoneum is the Veress needle.

A Veress needle comprises a two millimeter hollow bore needle with an apertured blunt stylet slidably disposed within the needle. The blunt stylet is spring loaded such that once the Veress needle has penetrated the tough fascial layer of the abdomen, the spring-loaded blunt stylet pops out from within the hollow needle, and an audible click can be heard. The blunt stylet extends beyond the sharp tip of the needle thus ostensibly protecting internal organs from being stabbed by the needle tip.

Correct placement of the needle can be verified by a number of different means. For example, a syringe of saline can be attached to the Veress needle, which has a luer lock at one end, and a small amount of the saline can be injected into the peritoneum. Fluid is then aspirated back out of the peritoneum. If blood is aspirated, it suggests misplacement of the needle and probable damage to an organ or vessel. The Veress needle is usually withdrawn and repositioned, followed thereafter by further testing to assure proper placement. Aspiration of yellowish fluid indicates penetration of the bowel. Again, the Veress needle must be withdrawn and repositioned. If difficult injection of saline followed by little or no aspiration is encountered, the result suggests that the needle is embedded within omentum. Aspiration of clear saline indicates a correct placement within the peritoneal cavity.

After correct placement of the Veress needle has been assured, an insufflator machine is connected to the luer lock of the Veress needle and gas is pumped into the peritoneal cavity. The Veress needle is then withdrawn from the peritoneal cavity. A cannula is inserted into the peritoneal cavity, either through another incision or through the same incision used to create the pneumoperitoneum. The cannula is placed in order to accommodate the insertion of optical and other equipment therethrough.

When using the incision through which the insufflation needle was placed, the incision must be enlarged with a scalpel to accommodate a 5 mm to 11 mm trocar. Trocars used for this procedure typically comprise a hollow-bore cannula with a sharp, pointed stylet slidably disposed therewithin. The tip of the stylet may be either a multi-faceted bevel or conical shape. The tip of the trocar is inserted into the now enlarged incision, and is forced through the underlying fascial layer and peritoneum of the abdomen using a downward pressure and drilling motion. The connective tissue of the fascia and peritoneum underlying the abdominal wall is so tough that a significant amount of force must be applied in order to achieve penetration of the tissue.

Unlike a Veress needle, trocars used in this procedure typically are not designed to shield the tip of the stylet once the stylet has penetrated the peritoneum. As a result of the intense drilling motion required to penetrate the peritoneum, the stylet can inadvertently puncture an organ or vessel upon entering the peritoneal cavity. Ethicon Company manufactures a disposable trocar with a plastic shield which covers the exposed tip of the stylet once the stylet has penetrated the peritoneum. Another frequently encountered problem of inserting a trocar through the tough fascial layer is that the elastic fascia may only stretch, similar to the head of a drum, and may resist penetration.

After the trocar has penetrated the peritoneum, the stylet is removed. The laparoscope is then inserted through the cannula portion of the trocar which remains in the abdominal wall and the peritoneal cavity is visualized. Auxiliary cannulas are positioned in other areas of the abdomen following the initial cannula placement. Positioning of the auxiliary cannulas relative to the abdominal region depends on many factors of pathology and morphology, and is assessed by viewing the peritoneal cavity through the laparoscope. Typically, auxiliary cannulas are placed in the area of the costal margin, and as such, care must be taken not to damage the epigastric vessels when placing the trocars. The auxiliary cannulas are used for insertion of surgical equipment.

The gallbladder can be visualized by the laparoscope placed through the first cannula and manipulated by the surgical instruments placed through the auxiliary cannulas. The gallbladder is excised from its position proximate the liver and is removed through the cannula inserted at the umbilicus. Each cannula is removed from its respective incision site, the peritoneal cavity is desufflated, and the incisions are sutured. The above-described techniques of laparoscopic cholecystectomy are well-known in the art and are more fully described in Berci, G. & Cuschierei, A., *Practical Laparoscopy*, Bailliere Tindall, 1986, p. 1–93; and *Laparoscopy For the General Surgeon-Laparoscopic Cholecystectomy and Appendectomy*, Karl Storz GmbH & Co., 1990.

From the above description, it can be appreciated that the method presently used for placing the insufflation equipment and for placing the trocars, or cannulas, into the peritoneal cavity presents a great deal of risk from inadvertent puncture to internal organs or vessels.

SUMMARY OF THE INVENTION

A hollow bore needle having a small gauge dimension is inserted into the peritoneum following the making of an initial incision into the abdominal wall. Insertion of a smaller gauge needle facilitates insertion of the needle through the tough fascial and peritoneal layers. Additionally, a smaller gauge needle reduces the chance of injuring any organs or vessels within the peritoneal cavity.

Proper placement of the needle in the peritoneum may be determined by any of several conventional methods. Once correct placement is assured, a pneumoperitoneum should be established. The pneumoperitoneum may be created by introducing gas into the peritoneal cavity through the needle. In one embodiment, insufflation, or introduction of gas into the peritoneal cavity, takes place through the needle inserted through the peritoneum. Alternatively, insufflation may take place through an apertured catheter inserted into the aperture after the needle has been removed from the aperture. Alternatively, insufflation may take place through a cannula placed through the aperture after removal of the needle from the aperture.

Following establishment of the pneumoperitoneum, the aperture formed in the abdominal wall is widened to receive a cannula through which a laparoscope or surgical equipment may be placed. The size of the aperture in the abdominal wall is increased by use of dilation means threaded over the guidewire and inserted into the peritoneal cavity. The dilation means may be one cannula having a tapered end which increases in diameter from about one millimeter to about twelve millimeters. In a preferred embodiment, the dilation means is a number of dilators or cannulas having tapered ends and incrementally larger diameters one from another.

When the aperture in the peritoneum has been dilated to a suitable size, a cannula sized to fit over the dilation means is placed over the dilation means and is inserted into the peritoneal cavity. The dilation means is then removed from within the cannula and from about the guidewire. The guidewire is then removed from within the peritoneal cavity and from within the cannula. A laparoscope or surgical instruments may then be placed through the cannula. At least two other apertures are formed through the abdominal wall following the method of the invention. Other surgical equipment is placed through the collateral apertures formed in the abdominal wall in order to perform the laparoscopic surgery.

Use of a small gauge needle to invade the peritoneal cavity has the significant advantage of reducing the occurrence of stab wounds to internal organs and vessels. A small needle also significantly facilitates penetration of the fascial layers thereby reducing appreciably the likelihood of inadvertent punctures. In the event that stab wounds should occur, the trauma to the organ or vessel is far less severe than that which is experienced with the presently used insufflator needles and trocar devices, and such small wounds tend to heal quickly without further medical attention. The use of a blunt-ended guidewire facilitates the safe dilation of the aperture since no organs or vessels can be damaged by the guidewire.

A kit comprising the components necessary for carrying out the method is provided. Included in the kit are a needle, guidewire, dilation means, cannulas of varying sizes, and suturing materials.

DETAILED DESCRIPTION OF THE PREFERRED EMBODIMENTS

The method of this invention begins with the preparation of the patient for surgery. The patient may first be positioned on the operating table in a manner most conducive to the surgical procedure to be performed. For cholecystectomy and other surgeries of the abdomen, a patient is typically placed in what is known in the art as a Trendelenburg position. A Trendelenburg position optimizes the arrangement of the internal organs by means of gravitational force, and presents the surgeon with the best operating position. The patient is then draped, and the site for incision is prepared by sterilization techniques well-known in the art.

For laparoscopic procedures, a pre-sedated patient is typically given a local anesthetic in the area of the incisions to be made. Laparoscopic procedures can also be performed under general or regional anesthetic. After anesthetization has taken place, the surgeon can begin the procedure of the invention.

Prior to performing laparoscopic surgery, a pneumoperitoneum must be created by insufflation of the peritoneal cavity. Insufflation is the introduction of gas into the peritoneal cavity for the purpose of creating a space within which surgical equipment may be passed. Insufflation takes place through an apertured needle inserted into the peritoneal cavity. Entry into the peritoneal cavity for the purpose of establishing the pneumoperitoneum typically takes place in close proximity to and either slightly above or below the umbilicus because of the thinness of the abdominal wall in that area.

Figure 1:
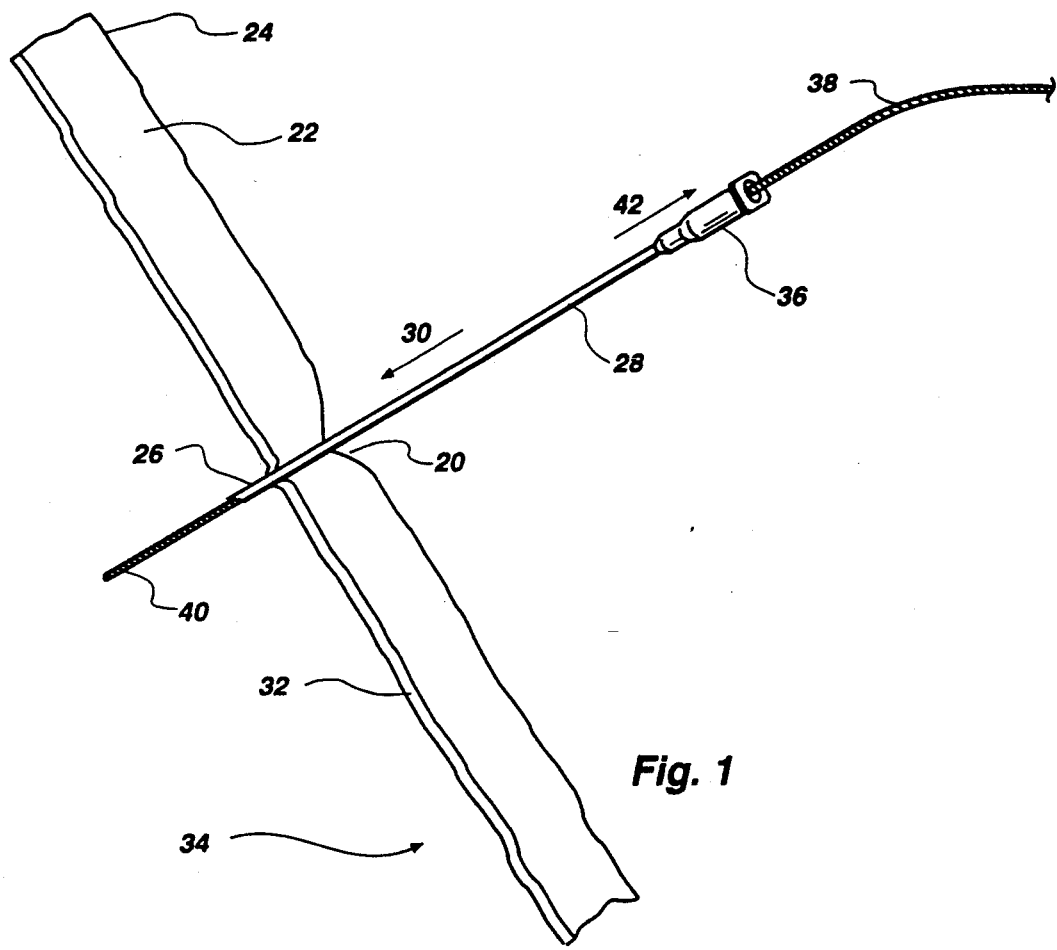
FIG. 1 is a perspective view of the placement of a needle and guidewire through the peritoneum of the abdominal wall, shown in cross-section.

Referring to FIG. 1, an incision 20 approximately one centimeter in length is made through the dermal layers 22 of the abdominal wall 24. The tip 26 of a hollow bore needle 28 is positioned within the incision 20 and is urged downwardly, in direction 30, until the tip 26 of the needle 28 penetrates the tough fascia and peritoneum 32 underlying the tissue of the abdominal wall. The urging of the needle 28 into the peritoneal cavity, generally at 34, should cease when the surgeon senses that the tip 26 of the needle 28 has penetrated through the elastic peritoneum 32 which is manifested by a sudden loss of resistance against the tip 26 of the needle caused by the tough fascial layer. In a preferred embodiment, the needle used for this procedure is an 18-gauge needle. A small needle, such as an 18-gauge needle, facilitates piercing the tough fascial layer and peritoneum, and eliminates the need to apply excessive pressure with a drilling motion to insert the needle. This further reduces the possibility of puncturing an organ or vessel within the peritoneal cavity.

Once the tip 26 of the needle 28 has been positioned within the peritoneal cavity 34, the correct placement of the needle can be evaluated by any of a number of methods. One method is to attach to the hub 36 of the needle 28 a syringe (not shown) half filled with saline. Saline solution is then injected into the peritoneal cavity, followed by aspiration of fluid from within the cavity. If the aspirated solution is clear, the needle may be assumed to be correctly positioned within the peritoneal cavity, and the syringe of saline may be removed from the hub 36 of the needle 28.

The peritoneal cavity may then be insufflated in order to create the pneumoperitoneum. A tube from an insufflator machine can be attached to the hub 36 of the needle 28, and gas can be introduced into the peritoneal cavity through the hollow needle 28. In a preferred embodiment, a guidewire 38 is inserted through the hollow bore of the needle 28 until the rounded, blunt end 40 of the guidewire is positioned within the peritoneal cavity 34. The needle 28 is then removed from within the peritoneal cavity 34, and is withdrawn from about the guidewire 38 in direction 42.

Figure 2:
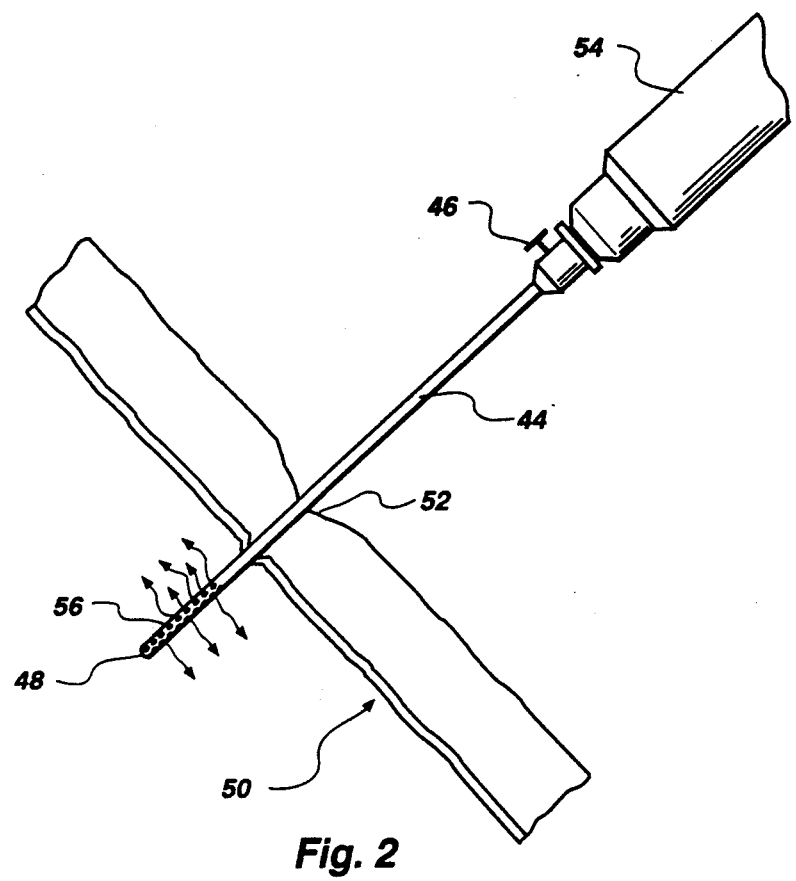
FIG. 2 is a perspective view illustrating insufflation.
Figure 3:
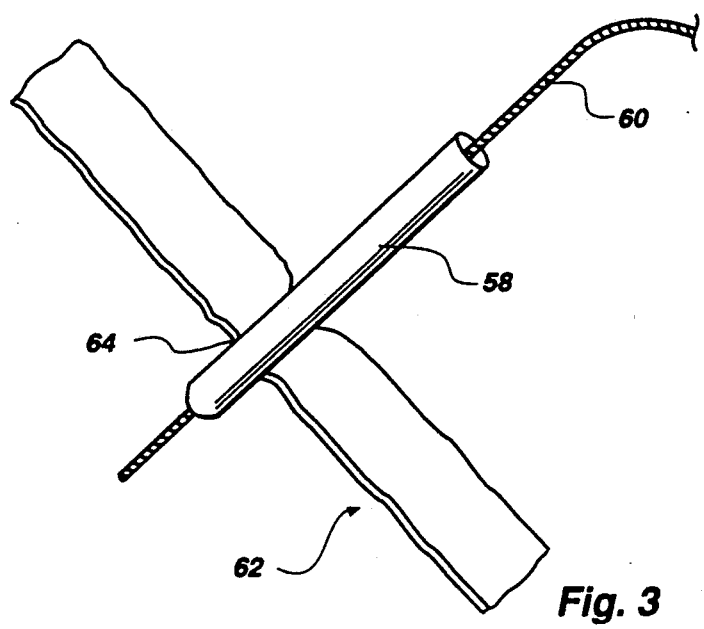
FIGS. 3 and 4 are perspective views of the dilators placed through the aperture.

An apertured hollow catheter 44, as shown in FIG. 2, having an appropriate luer lock 46 or similar connector means at one end is placed over the guidewire (not shown) and urged downwardly into the incision 52 until the tip 48 of the catheter 44 is disposed within the peritoneal cavity 50. The guidewire is then removed from within the catheter 44, and an insufflation hose 54 is attached via the luer lock or connector means 46 of the catheter for insufflation of the peritoneal cavity. Gas is introduced into the peritoneal cavity from a source of gas, and enters into the peritoneal cavity through the apertures 56 formed in the catheter 44. Typically, the gas is $CO_2$ provided from an insufflator machine. Gas is introduced into the peritoneal cavity until an appropriate level of pressure has been achieved. Typically, the level of pressure to be attained is 12 mm Hg, but the level of pressure required may be affected by the morphology of the patient. Once the pneumoperitoneum is established, the guidewire is reinserted into the catheter 44 used for insufflation, and the catheter is removed from within the peritoneal cavity.

If the needle 28 is used to insufflate the cavity, the insufflator hose is disconnected from the hub 36 of the needle 28 and the guidewire 38 is inserted through the needle 28 until the rounded blunt end 40 of the guidewire is positioned within the peritoneal cavity 34. The needle 28 is then removed from the peritoneal cavity 34 and from about the guidewire 38.

Dilation means is then placed over the guidewire and is urged downwardly through the aperture in the abdominal wall to increase the diameter of the aperture. In one embodiment, the dilation means is a number of cannulas or dilators, each having a tapered end. The dilators have incrementally different diameter sizes from each other and range from a dilator having a diameter of about one millimeter to a dilator having a diameter of about twelve millimeters. The dilators are sized in length to extend from exterior the abdominal wall to interior the peritoneal cavity. Additionally, the dilators vary in length one from the other, and each is sized in length to be inversely proportional to its diameter. In other words, a dilator having a one millimeter diameter is longer in length than a two millimeter dilator, which is longer in length than a three millimeter dilator. The variability of length between dilators will be obvious from the disclosure below.

Figure 4:
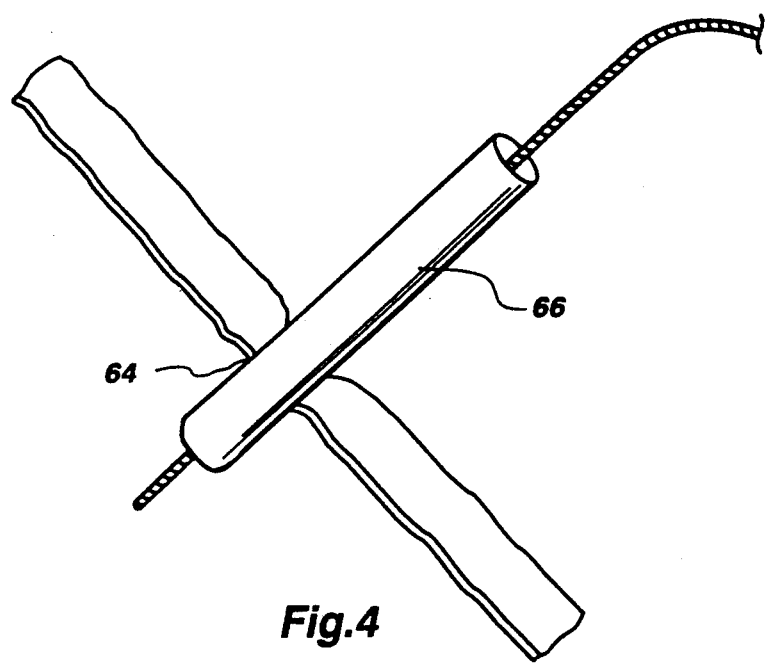
Figure 5:
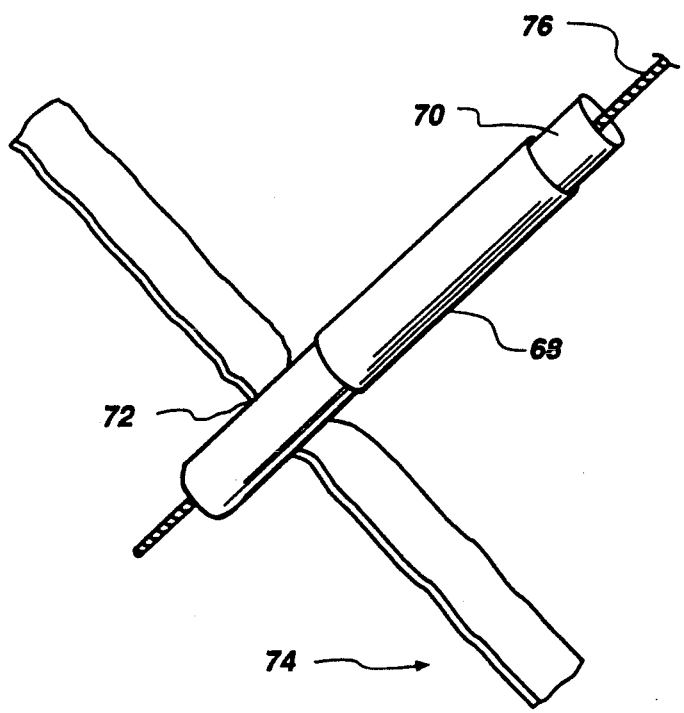
FIG. 5 is a perspective view illustrating placement of a cannula.
Figure 6:
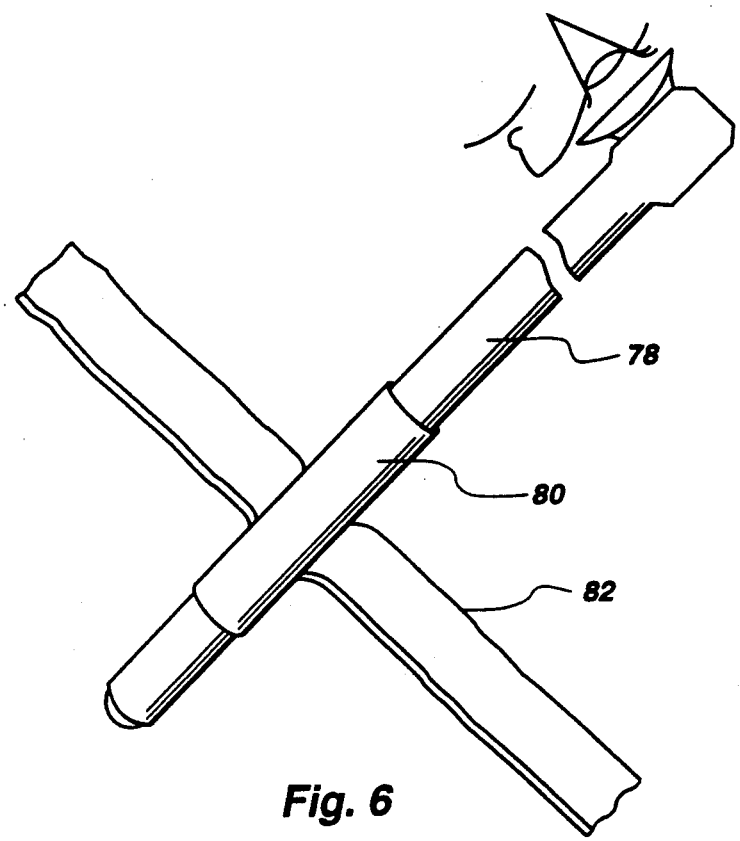
FIG. 6 is a perspective view illustrating placement of laparoscopic equipment.

In one embodiment illustrated in FIGS. 3 through 6, a small-diameter dilator 58 is first placed over the guidewire 60 positioned within the peritoneal cavity 62 and is inserted into the aperture 64 to increase its cross section. The small-diameter dilator 58 is then removed from the aperture 64, and a dilator having a slightly larger diameter is placed over the guidewire and is inserted into the aperture. The second dilator is then removed from the aperture and the guidewire, and a third dilator having yet a larger diameter is placed over the guidewire and inserted into the aperture. Each successive dilator inserted into the aperture serves to increase the size of the aperture formed in the peritoneum by the initial needle puncture. Referring to FIG. 4, a desired size of aperture 64 is eventually achieved by placement in the aperture 64 of a large-diameter dilator 66. Referring to FIG. 5, a cannula 68 sized to fit over the dilator 70 last inserted into the aperture 72 is placed over the last dilator 70 and is urged into the peritoneal cavity 74. The last dilator 70 is then removed from within the cannula 68, and the guidewire 76 is removed from within the cannula 68 and the peritoneal cavity 74. Laparoscopic equipment 78 is then inserted through the cannula 80 positioned through the abdominal wall 82, as shown in FIG. 6.

Figure 7:
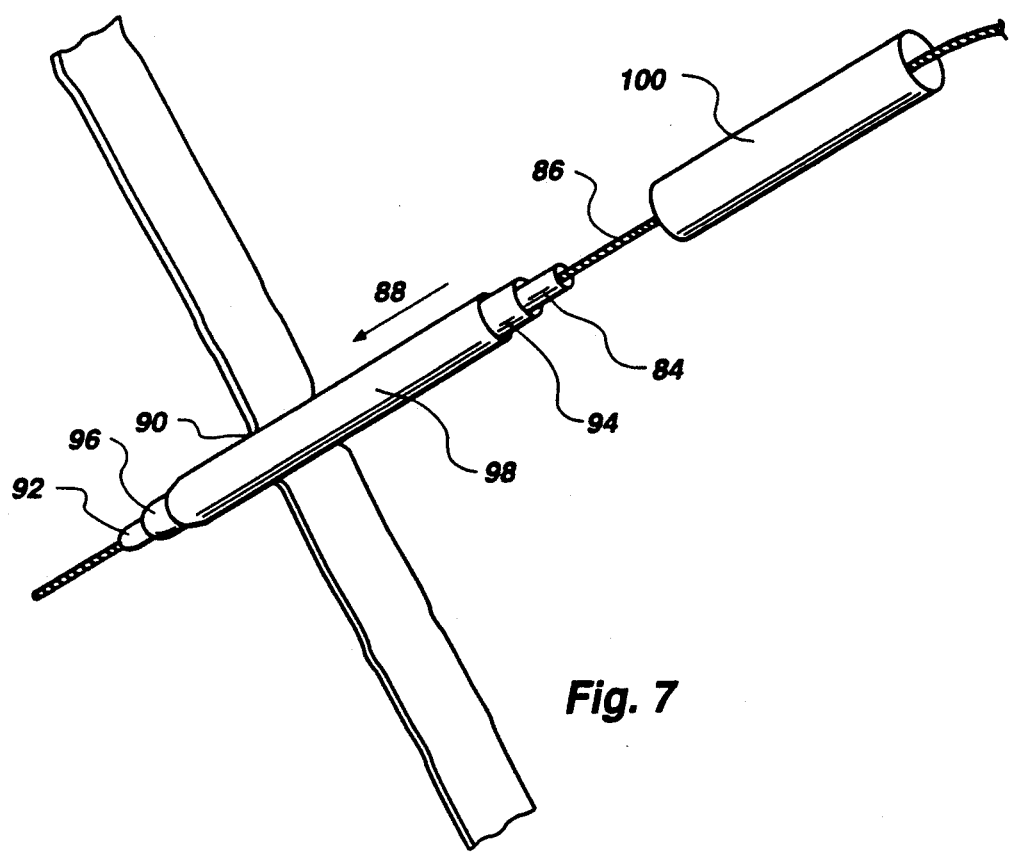
FIGS. 7–9 are perspective views illustrating alternative embodiments of the invention.

In an alternative embodiment, as illustrated in FIG. 7, a first small-diameter dilator 84 is threaded over the guidewire 86 and is urged in direction 88 into the aperture 90 in the abdominal wall until the tapered tip 92 is inserted through the aperture 90. A second dilator 94 having a larger diameter is placed over the first dilator 84 and is urged in direction 88 until the tapered tip 96 thereof is inserted into the aperture 90. A third dilator 98 is placed over the second dilator 94 followed by further dilators until the aperture 90 has attained a desired cross section. A cannula 100 sized to fit over the nested dilators is selected. The cannula 100 is placed over the nested series of dilators and is urged into the peritoneal cavity. The dilators 84,94, and 98, nested one inside the other, are then removed from within the cannula 100 and from within the peritoneal cavity. The guidewire 86 is then removed from within the peritoneal cavity.

Figure 8:
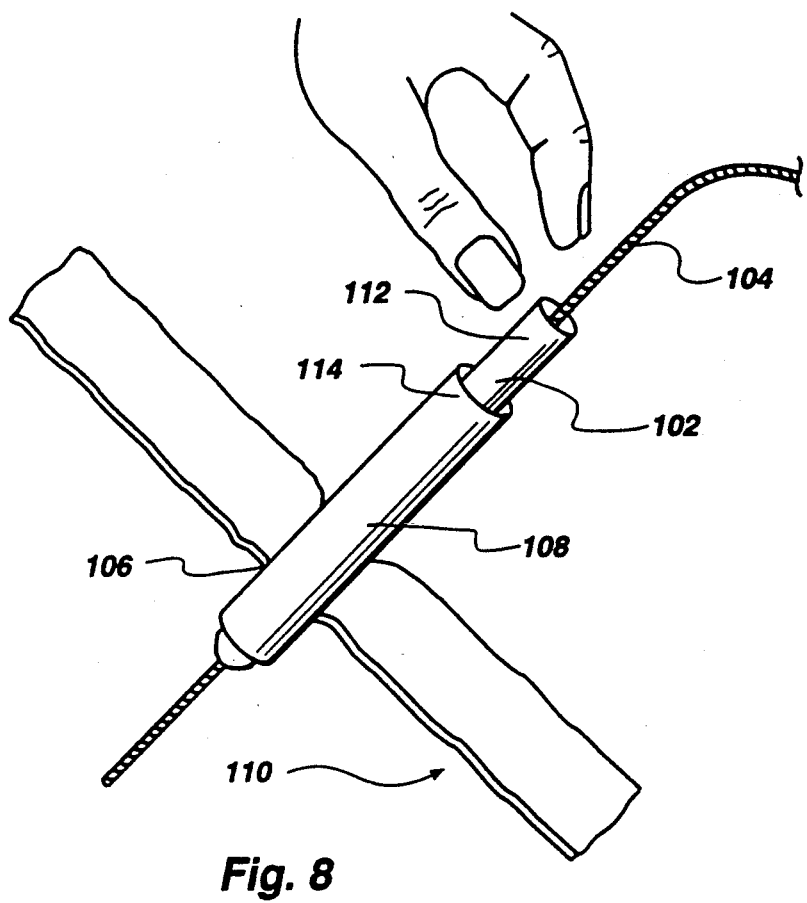

In another alternative embodiment illustrated in FIG. 8, a first small-diameter dilator 102 is threaded over the guidewire 104 and into the aperture 106 followed by placement of a second larger-diameter dilator 108 thereover. The first dilator 102 is then removed from the peritoneal cavity 110 and from within the second dilator 108 by grasping the upper portion 112 of the first dilator 102 which extends above the upper edge 114 of the second, shorter dilator 108. A third dilator (not shown) having a larger diameter than the second dilator 108 may then be placed over the second dilator 108 and inserted through the aperture 106. The second dilator 108 is then removed from within the third dilator and from the aperture by grasping the upper portion 114 of the second dilator 108 which extends above the upper edge of the third dilator. A subsequent dilator or dilators may be placed over the remaining dilator and the innermost dilator removed, as described above, until the aperture has reached a desired cross section. A cannula sized to fit over the dilator last positioned in the aperture is placed thereover and is urged into the peritoneal cavity. The last dilator is removed from within the cannula followed by removal of the guidewire from within the cannula and the peritoneal cavity.

The number and size of dilators threaded onto the guidewire is determined by the cross section of aperture needed for insertion of a laparoscope or other surgical instrumentation. The diameters of the dilators may range from about one millimeter to about twelve millimeters. The increments of increase between successive dilators may be between about one millimeter and about three millimeters. Thus, a series of dilators increasing in diameter by one millimeter increments would contain twelve dilators, each one larger than the prior one by one millimeter; similarly, a series of dilators increasing in diameter by two millimeter increments may contain six dilators having diameters of one, three, five, seven, nine, and eleven millimeters, respectively. A series of dilators may vary in number, and may increase in diameter by varying increments. It is only necessary that the dilators used increase the cross section of the aperture gradually.

Figure 9:
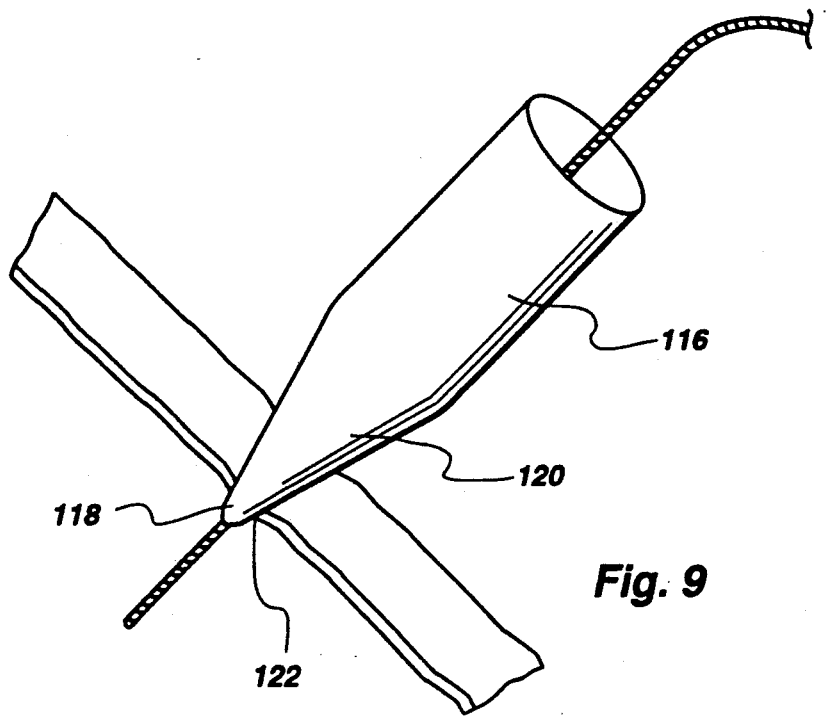

In an alternative embodiment, as shown in FIG. 9, the dilation means may be a single dilator 116 which gradually increases in diameter from approximately one millimeter at its proximal tip 118 to approximately twelve millimeters at its midpoint 120. As the dilator 116 is inserted into the aperture 122 formed through the peritoneum, the cross section of the aperture is gradually increased to a desired size. The dilator 116 can then be removed from the aperture 122 and a cannula can be placed within the aperture.

In an alternative embodiment of the invention, the needle is inserted through the abdominal wall and into the peritoneal cavity. The guidewire is then inserted through the needle and into the peritoneal cavity. The needle is removed from within the peritoneal cavity and dilation of the aperture made by the needle through the peritoneum proceeds as described above. When dilation of the aperture has proceeded to an appropriate diameter, a cannula is placed over the last dilator and is inserted into the peritoneal cavity. Insufflation then takes place through the cannula by attachment of a source of gas to the cannula.

A laparoscope may be inserted through the first cannula inserted in the area of the umbilicus. At least two other cannulas are placed in the abdominal wall of the patient following the procedure outlined above. Typically three other cannulas are placed in the abdominal wall of the patient in order to fully access and manipulate the internal organs as required by the surgery to be performed. The subsequently-placed cannulas are typically used for insertion of equipment for manipulating the internal organs, while the first cannula is used for placement of a laparoscope into the peritoneal cavity. In some surgical procedures, such as cholecystectomy, the cannulas are used as portals for removal of the excised organ from the peritoneal cavity.

After the surgical procedure has taken place, the equipment for manipulating the internal organs is removed from the subsequently-placed cannulas. Those cannulas are then removed from the abdominal wall. The laparoscope is then removed from the first cannula. The pneumoperitoneum is desufflated by removing the gas from the peritoneal cavity, and the first cannula is removed from the abdominal wall. The three incisions are then sutured to close.

Figure 10:
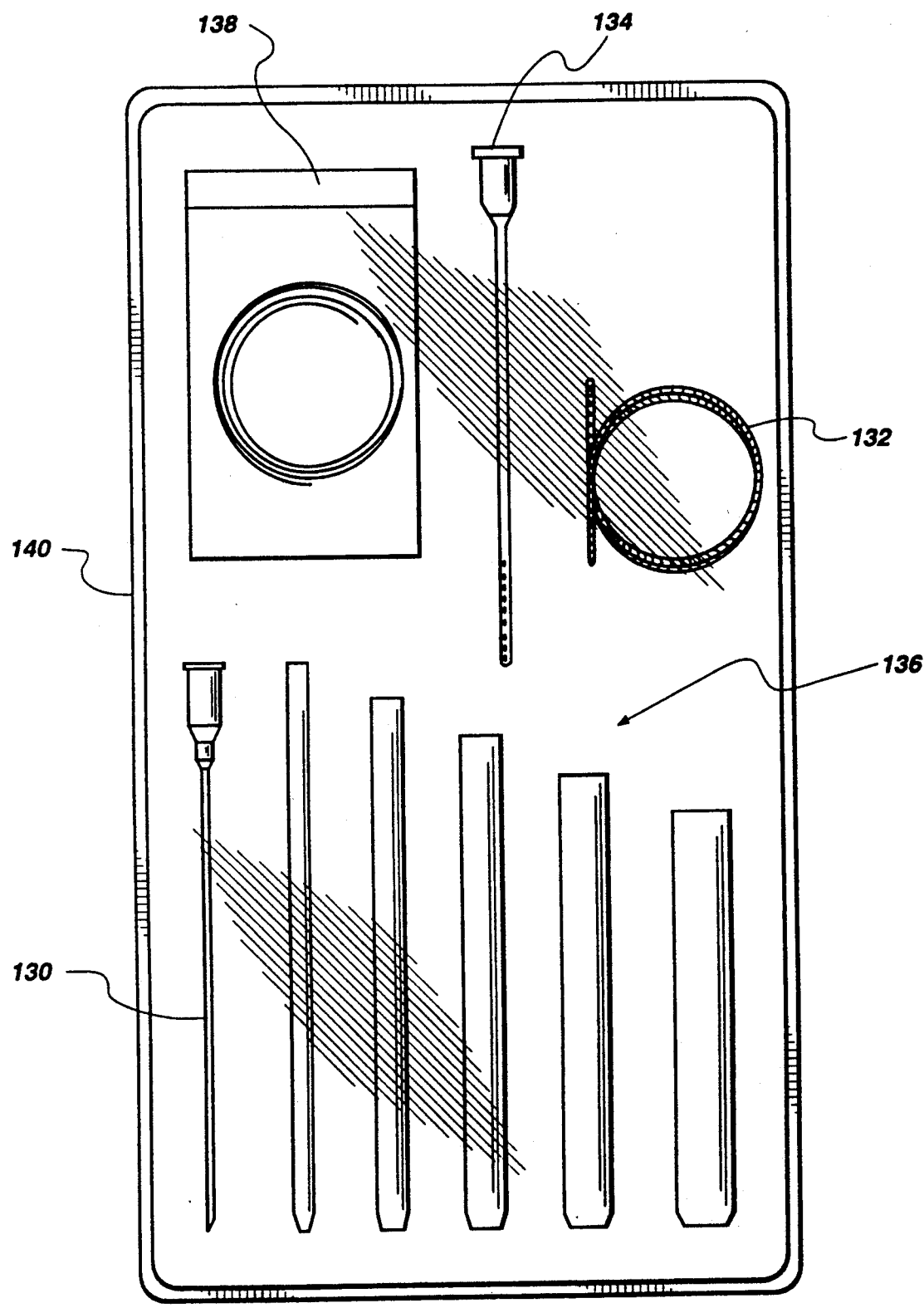
FIGS. 10 and 11 are plan views of alternative kits of the invention.

The materials and equipment necessary for carrying out the method of the invention are presented for use in the form of a kit. As illustrated in FIG. 10, the kit for performing the method may include a needle 130, a blunt-ended guidewire 132, an apertured catheter 134 for establishing the pneumoperitoneum, a series of dilators, generally at 136, and materials for suturing incision sites 138. All components are housed within a package 140 sized to receive the components required for the procedure. Thus, a surgeon may have at the ready all materials necessary for placing cannulas through the abdominal wall for insertion of laparoscopic equipment into the peritoneal cavity.

Figure 11:
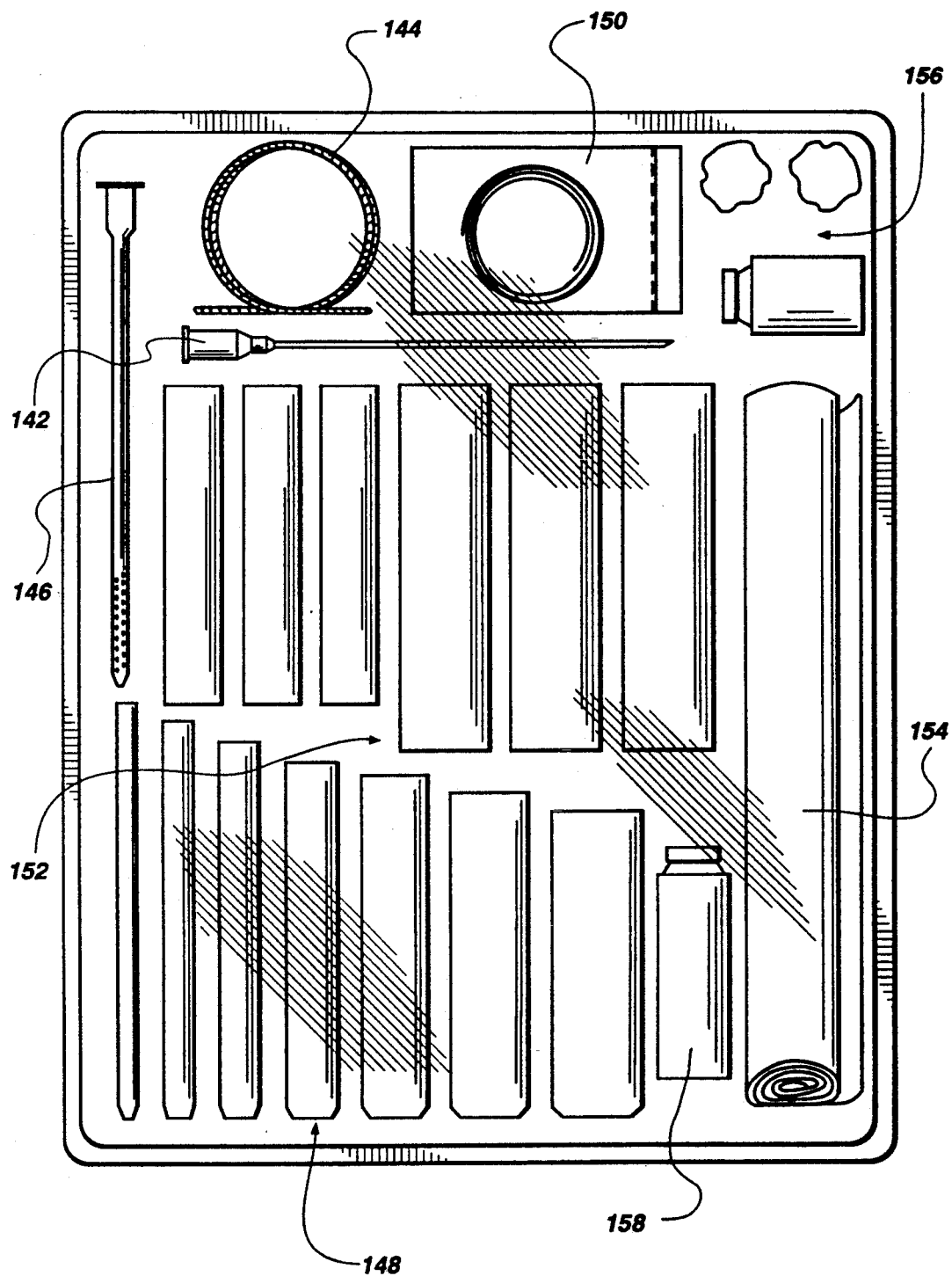

As shown in FIG. 11, the kit for performing the method of this invention, in addition to providing the needle 142, guidewire 144, apertured catheter 146, dilators 148, and suturing materials 150, may include a number of cannulas, generally at 152, which vary in size, draping materials 154, sterilization materials, generally at 156, and materials for anesthetization 158.

The foregoing disclosure of the invention presented herein is by way of example only and is not intended to limit the scope of the invention as defined by the claims which follow.

What is claimed is:

1. A method for performing surgical procedures within the peritoneal cavity of a patient said method comprising:
   providing means for making an incision in a patient;
   making an incision through the dermal layers of the abdominal wall of said patient;
   providing a needle having a hollow bore, a proximal end having a sharp tip, and a distal end opposite said proximal end, said needle being sized in length to extend from exterior said abdominal wall to interior the peritoneal cavity of said patient;
   positioning the tip of said needle within said incision;

urging said tip of said needle downwardly into said incision until said tip penetrates the peritoneum of said abdominal wall and enters said peritoneal cavity forming an aperture through said peritoneum;

providing a guidewire sized in cross section to fit within said hollow bore of said needle and sized in length to extend from said distal end of said needle to interior said peritoneal cavity, said guidewire having a proximal end with a rounded tip and a distal end;

urging said proximal end of said guidewire through said hollow bore of said needle until said proximal end of said guidewire is disposed within said peritoneal cavity;

removing said needle from within said peritoneal cavity and from about said guidewire;

providing a plurality of dilators for enlarging said aperture which are sized in diameter to be sequentially larger such that said dilators may be nested one inside another, each said dilator being sized in length to be inversely proportional to the diameter thereof such that dilators of smaller diameter and greater length provide a portion left unexposed by an overlying dilator which may be grasped to remove said smaller dilator from within said overlying dilator, each said dilator being sized in length to extend from exterior said abdominal wall to interior said peritoneal cavity, and each said dilator having a tapered interior end;

positioning a dilator of smaller diameter over said guidewire urging said tapered interior end of said dilator through said aperture and into said peritoneal cavity followed by placement of a dilator of greater diameter thereover and through said aperture;

removing one or more dilators from said guidewire while leaving in place the last positioned dilator;

providing a cannula sized to fit over said last placed dilator and within said aperture following dilation of said aperture;

positioning said cannula over said last placed dilator and urging said cannula through said aperture and into said peritoneal cavity;

removing all remaining dilators from within said cannula and from about said guidewire;

removing said guidewire from within said cannula; and providing and inserting through said cannula means for performing surgery within said peritoneal cavity.

2. The method according to claim 1 further comprising providing and positioning an apertured cannula over said guidewire after removing said needle from within said peritoneal cavity and urging said apertured cannula into said peritoneal cavity, and further comprising removing said guidewire from within said apertured cannula, connecting a source of gas to said apertured cannula, and introducing gas into said peritoneal cavity through said apertured cannula to form a pneumoperitoneum, then reinserting said guidewire through said apertured cannula and removing said apertured cannula from within said peritoneal cavity.

3. The method according to claim 2 wherein said needle has means adapted thereto at said distal end in communication with said bore for reflecting the pressure of a fluid in said bore, and wherein said method further comprises evaluating placement of said needle following entry of said tip into said peritoneal cavity.

4. The method according to claim 1 further comprising connecting a source of gas to said distal end of said needle and introducing gas into said peritoneal cavity through said aperture to form a pneumoperitoneum.

5. The method according to claim 1 wherein said diameters of said dilators range from about one millimeter to about twelve millimeters.

6. The method according to claim 5 wherein said positioning of said dilator means further comprises positioning a dilator having a smaller diameter over said guidewire and urging said dilator into said peritoneal cavity, then removing said dilator from within said peritoneal cavity and positioning a dilator having a larger diameter than that of the previously positioned dilator over said guidewire and urging said dilator into said peritoneal cavity.

7. The method according to claim 5 wherein said positioning of said dilator means further comprises positioning a first dilator having a smaller diameter over said guidewire and urging said dilator into said peritoneal cavity, then positioning a second dilator having a larger diameter than that of the previously positioned dilator over said first dilator and urging said second dilator into said peritoneal cavity, then removing said first dilator from within said second dilator and from within said peritoneal cavity.

8. The method according to claim 5 wherein said positioning of said dilator means further comprises positioning a dilator having a smaller diameter over said guidewire and urging said dilator into said peritoneal cavity, then positioning another dilator having a larger diameter than that of the previously positioned dilator over said previously positioned dilator and urging said dilator into said aperture, then removing said dilators from said peritoneal cavity.

9. The method according to claim 1 further comprising providing a source of gas and attaching said source of gas to said cannula after said dilation means and said guidewire are removed from within said cannula.

10. A peritoneal cannula placement kit comprised of:
an openable package having a bottom, top, and sides defining a space therewithin sized to receive components for surgically placing a cannula through the abdominal wall of a patient for the purpose of performing laparoscopic surgery therethrough, said components including:

needle means for puncturing the fascia and peritoneum underlying the dermal layers of the abdominal wall of the patient in order to form an aperture therethrough;

guidewire means for maintaining said aperture and for guiding hollow cylindrical components through said aperture;

a plurality of dilators for dilation of said apertures, said dilators being sized in diameter to fit over said guidewire means and sized in length to extend from exterior the abdominal wall of a patient to interior the peritoneal cavity of said patient, said diameters of said dilators varying each from the other and ranging in diameter size from about one millimeter to about twelve millimeters each said dilator being sized in length to be inversely proportional to the diameter thereof;

apertured cannula means for creating a pneumoperitoneum by insufflation; and suturing means for surgically closing incisions made by said means for making incisions.

11. The kit of claim 10 wherein said contents further include a plurality of cannulas sized to fit over said dilators and sized to extend from exterior said abdominal wall to interior said peritoneal cavity.

12. The kit of claim 11 wherein said contents further include:
- skin preparation means to clean and sterilize the area of the abdomen to be incised;
- anesthetic means to anesthetize the patient; and
- draping means for positioning over the body area of the patient to be operated on.

13. A method for performing surgery within the peritoneal cavity of a patient, said method comprising:
- preparing the patient for surgery;
- providing means for making incisions into the dermal layers of said patient;
- making an incision through the dermal layers of the abdominal wall of said patient with said mean for making incisions;
- providing a needle having a hollow bore, a proximal end defining a tip, and a distal end opposite said proximal end;
- positioning the tip of said needle within said incision;
- urging said tip of said needle into said incision until said tip penetrates the peritoneum of said abdominal wall and enters the peritoneal cavity of said patient thereby forming a first aperture through said peritoneum;
- providing means for determining placement of said needle in said peritoneal cavity;
- determining said placement of said needle in said peritoneal cavity using said means for determining said placement;
- providing a guidewire sized in cross section to fit within said hollow bore of said needle and sized in length to extend from said distal end of said needle to interior said peritoneal cavity, said guidewire having a proximal end defining a rounded tip and a distal end;
- threading said guidewire through said hollow bore of said needle until said proximal end of said guidewire is disposed within said peritoneal cavity;
- removing said needle from within said peritoneal cavity and from about said guidewire;
- providing a cannula having a distal end and a proximal end in which are formed apertures;
- positioning said cannula over said guidewire and urging said apertured end of said cannula into said peritoneal cavity;
- removing said guidewire from within said cannula;
- providing a source of gas and a hose having connector means for connecting said source of gas to said distal end of said cannula;
- interconnecting said hose between said source of gas and said distal end of said cannula;
- introducing gas into said peritoneal cavity until sufficient pressure is attained within said peritoneal cavity to form a pneumoperitoneum;
- removing said hose from said distal end of said cannula;
- reinserting said guidewire through said cannula and into said peritoneal cavity;
- removing said cannula from within said peritoneal cavity;
- providing dilation means for dilating said aperture, said dilation means being sized in diameter to fit over said guidewire and sized in length to extend from exterior said abdominal wall to interior said peritoneal cavity;
- positioning said dilation means over said guidewire and urging said dilation means toward said aperture in said peritoneum until at least a portion of said dilation means enters through said aperture and extends into said peritoneal cavity;
- providing cannula means for forming an opening through said abdominal wall of said patient, said cannula means sized to fit over said dilation means;
- positioning said cannula means over said dilation means and urging said cannula means into said aperture formed in said peritoneal cavity;
- removing said dilation means from within said peritoneal cavity and from within said cannula means;
- removing said guidewire from within said cannula means;
- providing a laparoscope for visualizing said peritoneal cavity and its contents, said laparoscope having a proximal end comprising a lens and a distal end having means for viewing;
- inserting said laparoscope through said cannula until said proximal end of said laparoscope is positioned within said peritoneal cavity;
- inserting a second cannula and a third cannula into said abdominal wall through a second and third aperture made in said abdominal wall, respectively;
- providing surgical equipment for manipulation of the internal organs of said patient;
- inserting said surgical equipment for manipulation through said second and third cannulas and manipulating said internal organs in order to access the internal organs of said patient;
- providing surgical equipment for performing surgery within said peritoneal cavity;
- performing surgery within said peritoneal cavity;
- removing said surgical equipment for manipulation and said surgical equipment for performing surgery from said second and third cannulas;
- removing said laparoscope from said first aperture;
- removing said second and third cannulas from said abdominal wall;
- removing said gas from said peritoneal cavity through said first aperture;
- providing suture materials for suturing said apertures and said incisions; and
- suturing closed said apertures and said incisions.

14. The method according to claim 13 wherein preparing said patient for surgery further comprises:
- positioning said patient in a position to optimize gravitational force upon the internal organs of said patient;
- providing draping means for covering said patient during surgery;
- draping said patient with said draping means to substantially cover said patient while leaving the areas for incision undraped;
- providing anesthetic means for anesthetizing said patient; and
- anesthetizing said patient using said anesthetic means.

15. A method for performing surgical procedures within the peritoneal cavity of a patient said method comprising:
- providing means for making an incision in a patient;
- making an incision through the dermal layers of the abdominal wall of said patient;
- providing a needle having a hollow bore, a proximal end having a sharp tip, and a distal end opposite said proximal end, said needle being sized in length to extend from exterior said abdominal wall to interior the peritoneal cavity of said patient;

positioning the tip of said needle within said incision;

urging said tip of said needle downwardly into said incision until said tip penetrates the peritoneum of said abdominal wall and enters said peritoneal cavity forming an aperture through said peritoneum;

providing a guidewire sized in cross section to fit within said hollow bore of said needle and sized in length to extend from said distal end of said needle to interior said peritoneal cavity, said guidewire having a proximal end with a rounded tip and a distal end;

urging said proximal end of said guidewire through said hollow bore of said needle until said proximal end of said guidewire is disposed within said peritoneal cavity;

removing said needle from within said peritoneal cavity and from about said guidewire;

providing a dilator for dilating said aperture formed in said peritoneum, said dilator having a proximal end and a distal end and being sized in diameter to fit over said guidewire, being sized in length to extend from exterior said abdominal wall to interior said peritoneal cavity, and being tapered from said proximal end to said distal end to provide gradual and uniformly increasing enlargement of said aperture from about one millimeter to about twelve millimeters;

positioning said dilator over said guidewire, urging said proximal end through said aperture and into said peritoneal cavity;

providing a cannula sized to fit over said dilator and within said aperture following dilation of said aperture;

positioning said cannula over said dilator and urging said cannula through said aperture and into said peritoneal cavity;

removing said dilator from within said cannula and from about said guidewire;

removing said guidewire from within said cannula; and providing and inserting through said cannula means for performing surgery within said peritoneal cavity.

* * * * *